United States Patent [19]

Schnoring et al.

[11] 4,402,856

[45] Sep. 6, 1983

[54] MICROCAPSULES WITH A DEFINED OPENING TEMPERATURE, A PROCESS FOR THEIR PRODUCTION AND THEIR USE

[75] Inventors: Hildegard Schnoring, Wuppertal; Bruno Bömer; Manfred Dahm, both of Leverkusen, all of Fed. Rep. of Germany

[73] Assignee: Bayer Aktiengesellschaft, Leverkusen, Fed. Rep. of Germany

[21] Appl. No.: 251,673

[22] Filed: Apr. 6, 1981

[30] Foreign Application Priority Data

Apr. 26, 1980 [DE] Fed. Rep. of Germany ....... 3016170

[51] Int. Cl.³ .............................................. B01J 13/02
[52] U.S. Cl. .................................... 428/402.22; 8/526; 8/675; 71/DIG. 1; 252/174.13; 252/299.01; 252/358; 252/522 A; 424/33; 424/35; 424/37; 427/338; 428/402.22; 252/315.1; 252/315.3
[58] Field of Search .......................... 252/316; 427/338

[56] References Cited

U.S. PATENT DOCUMENTS

| | | | |
|---|---|---|---|
| 2,886,445 | 5/1959 | Rosenthal et al. | 426/5 |
| 3,687,865 | 8/1972 | Katayama et al. | 252/316 |
| 3,956,172 | 5/1976 | Saeki et al. | 252/316 |
| 4,082,688 | 4/1978 | Egawa et al. | 252/316 |

FOREIGN PATENT DOCUMENTS

| | | |
|---|---|---|
| 352686 | 3/1975 | Australia . |
| 646758 | 8/1962 | Canada ................................. 252/316 |
| 9413 | 9/1979 | European Pat. Off. . |
| 2441890 | 3/1975 | Fed. Rep. of Germany . |
| 2458879 | 6/1975 | Fed. Rep. of Germany . |
| 2515176 | 10/1975 | Fed. Rep. of Germany . |
| 2616418 | 11/1977 | Fed. Rep. of Germany . |
| 2734577 | 2/1979 | Fed. Rep. of Germany . |
| 3032616 | 3/1981 | Fed. Rep. of Germany . |
| 2232360 | 1/1975 | France . |
| 929405 | 6/1963 | United Kingdom ................ 252/316 |

OTHER PUBLICATIONS

Chemical Abstracts, Band 91, Nr. 4, 23, Jul. 1979, Seite 64, Nr. 22015, Seiffen-Ole-Fette-Wachse, Band 98, Nr. 26, Dec. 1972, Seiten 897–900.

Gustavson: "The Chemistry of Tanning Processes", Academic Press Inc., New York, (1956), pp. 153–156.

Primary Examiner—Richard D. Lovering
Attorney, Agent, or Firm—Felfe & Lynch

[57] ABSTRACT

Microcapsules having a defined release temperature and being formed of gelatin or a mixture of gelatin with gum arabic, carboxymethylcellulose and/or anionic polymers, the gelatin having been hardened with a natural and/or synthetic tanning agent and with a carbonyl compound, and the process for making said microcapsules.

18 Claims, No Drawings

MICROCAPSULES WITH A DEFINED OPENING TEMPERATURE, A PROCESS FOR THEIR PRODUCTION AND THEIR USE

The present invention relates to microcapsules which release the enclosed substance at a defined temperature, a process for the production of these microcapsules and their use for various purposes.

It is known that microcapsules which contain liquids, solids, emulsions or suspensions as the core material and of which the shell material consists of a high-molecular substance can be produced by complex coacervation, from DE-AS (German Published Specification) No. 1,122,495.

It is thus possible, for example, to produce such microcapsules by a procedure in which the shell substance is precipitated from an aqueous solution or colloid onto the core material, which is dispersed in this solution.

In general, first a dispersion (emulsion or suspension) of the desired core material and the aqueous solution of the shell substance is prepared. Coacervation is then initiated either by changing the pH value of the solution or by adding a precipitating agent, such as water or methanol causing the coacervate (which is the colloid-rich phase and is the shell substance) to separate out of the continuous phase of the dispersion and be deposited around the discontinuous phase (which is the core material).

This separating out of the coacervate around the discontinuous phase is always caused by the fact that the individual particles represent inhomogeneity points in the continuum of the colloidal solution and therefore act as condensation nuclei in the formation of the colloid-rich phase (the coacervate), so that a closed coacervate shell forms around the individual particles.

Shell materials which have been described for such coacervate systems are, inter alia, hydrophilic, film-forming colloids, such as a combination of acid-limed and alkali-limed gelatin or a combination of acid-limed gelatin and gum arabic (see DE-AS (German Published Specification) No. 1,122,495) and also mixtures of gelatin and anionic polymers, such as acrylamide/maleic acid copolymers and acrylamide/acrylic acid/maleic acid terpolymers (see DE-OS (German Published Specification No. 2,734,577). A decisive disadvantage of these known microcapsule suspensions is that they are not stable to storage at room temperature, but coagulate to form a jelly. At storage temperatures of below 10° C., the capsules indeed remain separate, but the shell materials disintegrate at elevated temperatures or when the pH value of the suspension changes, and the core material is not always released at the desired point in time and at the desired place.

Furthermore, it is also known that microcapsules with shells which consist of gelatin or contain gelatin can be hardened with the aid of various reagents.

Thus, for example, carbonyl compounds, such as formaldehye, glyoxal, glutarodialdehyde or pentane-2,3-dione, are suitable for irreversibly crosslinking, and hence for hardening wall materials based on gelatin, by the formation of covalent bonds. In general, a procedure is followed in which the hardening agent is added to the capsule suspension and the pH value of the suspension is then adjusted to a value favourable for the crosslinking reaction, for example to a pH value of between 9 and 10 when formaldehyde is used.

Microcapsule suspensions optimally hardened with carbonyl compounds do not release their core material in the presence of water even at temperatures of 100° C. and more. However, these hardened microcapsules also have the disadvantage that they do not release the core materials at a defined high temperature. Rather, the release temperature for the enclosed core material increases with the storage time. It is also not possible to suppress this undesired effect by separating off the aqueous phase by means of decanting or filtration and carefully washing the capsules.

The present invention provides microcapsules with a defined release temperature for the enclosed material. The microcapsules according to the invention are characterized in that the wall material consists of gelatin, which may be mixed with gum arabic, carboxymethylcellulose and/or anionic polymers, and the gelatin containing shell is hardened with a natural and/or synthetic tanning agent and with a carbonyl compound.

According to the present invention there is also provided a process for the production of the microcapsules according to the invention in which (a) gelatin, optionally mixed with gum arabic, carboxymethylcellulose and/or anionic polymers, is coacervated in an aqueous medium in the presence of a core material, by diluting, cooling and/or changing the pH value of the mixture, (b) after pre-hardening with a natural and/or synthetic tanning agent, which is to be carried out, in acid medium, the shells of the microcapsules thereby formed are hardened with a carbonyl compound in a weakly acid or basic medium under hardening conditions adjusted to correspond to the desired release temperature, and (c) finally, the microcapsule suspension thus obtained is either dried directly or the microcapsules are separated off from the liquid phase and then dried.

It has also been found that the microcapsules according to the invention can be employed for the most diverse purposes, depending on the nature of the core material contained therein.

Thus, depending on the core material, such microcapsules can be used, for example, in washing agents, bath additives, household agents, hygiene agents, cellulose nappies, dyestuffs, dispersions for the preparation of plastics, duplicating paper, textile auxiliaries or agents for the treatment of plants. The use of microcapsules of the present invention in washing agents or bath additives is particularly preferred.

Surprisingly, the microcapsules according to the invention have a defined opening temperature which does not change or changes only very slightly on storage. In view of the known state of the art, such properties could not be expected since, in the case of all chemically similar microcapsule suspensions which have already been described, the release temperature for the core material increases with the storage time.

The microcapsules according to the invention are distinguished by several advantages. Thus, they can be produced in a simple manner and can be stored without the temperature at which the core material is released changing substantially. In addition, the microcapsules according to the invention, which are present in pulverulent form, can be conveniently packed, transported and mixed with other powders and redispersed at any time.

A particular advantage is that the release temperature for the core material can be varied within wide limits, and adjusted to the particular level desired, by the choice of hardening conditions.

Possible gelatin wall-forming material in the production of the microcapsules according to the invention is preferably acid-limed and alkali-limed gelatin or a mixture of such gelatin with gum arabic, carboxymethylcellulose and/or an anionic, water-soluble polymer which consists of (A) a copolymer, the structural units of which consist to the extent of 65 to 90 mole %, relative to the polymer, of randomly distributed radicals of acrylamide and to the extent of 10 to 35 mole % of radicals of maleic acid or maleic anhydride, and which has an intrinsic viscosity $[\eta]$ of 0.05 to 1.0 [dl/g], and (B) a copolymer, the structural units of which consist of randomly distributed polymerized radicals of acrylamide, acrylic acid and maleic acid—the maleic acid radicals being at least partly present in salt form—and which has an intrinsic viscosity $[\eta]$ of 0.05 to 1.5 [dl/g] and contains a total of 65 to 90 mole %, relative to the polymer, of radicals of acrylamide and of acrylic acid, and 10 to 35 mole % of radicals of maleic acid, the weight ratio of (A):(B) being 1:2 to 20:1.

The gelatin wall-forming materials and their use for this purpose are known from DE-AS (German Published Specification) No. 1,122,495 and DE-OS (German Published Specification) No. 2,734,577.

In the process according to the invention any anionic polymers present are employed in the form of aqueous solutions which preferably contain 5 to 30% by weight, relative to the solution, of polymer.

Particularly preferred gelatin wall-forming materials are mixtures which contain gelatin, carboxymethylcellulose and/or gum arabic, and the water-soluble anionic polymers mentioned above as preferred.

Pre-hardening agents are employed in the process according to the invention. Natural tanning agents and synthetic tanning agent substitutes can preferably be used for this. Natural tanning agents which may be mentioned specifically are tannin, mimosa, quebracho and gallic acid. As synthetic tanning agent substitutes there may be mentioned specifically methylene-linked condensation products of a hydroxyarylsulphone and aromatic sulphonic acids, such as the product known by the Trade Mark "Tanigan" QF, and also methylene-linked condensation products of aromatic sulphonic acids, such as the products known by the Trade Marks "Tanigan" PR and "Tanigan" PT.

The natural tanning agents in most cases give rise to a more or less pronounced discoloration of the capsules, in addition to hardening. In contrast, the synthetic tanning agents lead to no discoloration or to only slight discoloration, of the capsule suspensions.

Possible carbonyl compounds, which are required as hardening agents in the process according to the invention, are all the sufficiently reactive aldehydes and ketones. Formaldehyde, glutarodialdehyde, glyoxal and pentane-2,3-dione are preferably used.

A large number of liquid or solid dispersible substances which are sparingly soluble or insoluble in water and are sufficiently stable to water can be microencapsulated by the process according to the invention.

Examples which may be mentioned are organic solvents, paraffin oils, perfume oils, silicone anti-foaming agents, phosphoric acid esters, liquid crystals, organic pigments, inks, disinfectants, detergent additives and agents for treating plants.

The process according to the invention is carried out in an aqueous medium.

In the process according to the invention, the coacervation is carried out either by diluting the reaction mixture, or by cooling the reaction mixture, or by changing the pH value of the reaction mixture, or by a combination of these measures. Preferred possible diluents in this context are water and/or water-miscible alcohols, such as methanol or ethanol. The pH value can be changed by adding acid or base, depending on the colloid used.

In the process according to the invention, the coacervation can be carried out within a relatively wide temperature range. In general, coacervation is carried out at temperatures between 0° C. and 80° C., preferably between 5° C. and 60° C.

The pre-hardening of the microcapsules is carried out in the process according to the invention in an acid medium. In general, the pre-hardening is carried out at pH values of between 3 and 6, preferably between 3.5 and 5.0.

The temperature can be varied within a certain range during pre-hardening. In general, pre-hardening is carried out at temperatures between 5° C. and 70° C., preferably between 20° C. and 50° C.

The hardening with carbonyl components is carried out in a basic or weakly acid medium. If the pre-hardened capsule suspension has a pH value in the acid range, the desired pH value is established by adding bases. Preferred possible bases for this are aqueous sodium hydroxide solution, aqueous potassium hydroxide solution and aqueous sodium carbonate solution.

In general, this hardening is carried out at pH values between 5.5 and 11.0, preferably between 6.0 and 10.0.

The temperature can be varied within a certain range during hardening. In general, hardening is carried out at temperatures between 0° C. and 70° C., preferably between 20° C. and 60° C.

The microcapsule suspensions which can be produced according to the invention are either dried directly or after separating off the microcapsules from the liquid phase. Direct separation can be carried out, for example, in a spray-drier or in a fluidized bed. The initial temperature of the product (temperature of the material to be dried) should always be at least 20° C. below the temperature at which the core material is released from the microcapsules according to the invention. As the drying time increases, the temperature of the material to be dried can be increased. In general, the final drying temperature of the microcapsules is 70° C.

It is also possible for the microcapsules to be first essentially separated off from the liquid phase, for example by decanting, and then to be dried, if appropriate after mixing with an agent which assists flow, such as highly dispersed silicic acid, barium stearate or chalk.

In carrying out the process according to the invention, the pre-hardening agent can be added during or after the coacervation. It is particularly advantageous to add the pre-hardening agent with the diluent, that is to say preferably with the water used for the dilution, since the amount of empty coacervate, that is to say wall material without enclosed core material, obtained in this procedure is particularly small.

If natural tanning agents are used as the pre-hardening agents, it must be ensured that the tanning agent is distributed very carefully and rapidly in the capsule suspension in order to prevent local over-hardening of capsules, because this leads to an undesirably wide range of opening temperature. When synthetic tanning agents are used as the pre-hardening agent, the mixing operation is not so critical.

The carbonyl component functioning as the actual hardening agent is added after the coacervation. The carbonyl component can be added either together with the pre-hardening agent or thereafter. It is preferable to add the carbonyl component after pre-hardening in a subsequent phase in which the capsule suspension is cooled to low temperatures, preferably between 5° C. and 10° C., or to add the carbonyl component when gelatinization of the coacervate shell has finished.

The hardening effect of the particular carbonyl component depends on the pH value of the capsule suspension. The optimum value in each case can be established by a few preliminary experiments. Thus, the most favourable pH range for glutarodialdehyde is between 6.0 and 10.0, while formaldehyde only exhibits a noticeable hardening effect above a pH value of 8. Hardening results which can be particularly easily reproduced are obtained when the hardening of the capsules is carried out in two stages, that is to say when the capsules are pretreated with a natural or synthetic tanning agent at pH values of below 6.0 before covalent crosslinking of the capsule shells with carbonyl compounds.

The microcapsules according to the invention release their core material in the presence of water or aqueous solutions in a defined, narrow temperature range (=opening temperature, release temperature). The opening temperature of the microcapsules can be adjusted in a controlled manner within a relatively wide range. In general, the opening temperature is in a certain narrow temperature range at temperatures between 30° C. and 150° C., preferably between 35° C. and 120° C. The particular opening temperature desired is achieved by hardening the microcapsule suspensions, after the coacervation, until the desired release temperature has been reached, and then drying the microcapsule suspensions. The opening temperature of the dried capsules is in general 2° to 5° C. greater than that of the capsule suspension (capsule slurry) before drying.

If a defined amount of a carbonyl hardening agent, such as formaldehyde or glutarodialdehyde, is allowed to act, at a certain pH value and at a certain temperature, on the microcapsule suspensions obtained after the coacervation, the release temperature for the core material increases as the action period of the hardening agent increases. For the same action period and hardening agent concentration, the release temperature increases within certain ranges as the pH value increases and the reaction temperature increases.

The temperature at which the microcapsules according to the invention release the core material can be determined in a simple manner. A procedure is followed in which, in a preliminary experiment, the core material is stained with a dyestuff which is soluble in oil but insoluble in water and is then encapsulated by the process according to the invention. After a short time, 20 ml of the hardened microcapsule slurry are introduced into 80 ml of demineralised water and the slurry is stirred for 5 minutes at a temperature significantly below the opening temperature to be expected. 1.5 ml of this capsule suspension are then introduced into a water-immiscible organic solvent, which has been warmed to 35° to 45° C., the mixture is shaken and, after the capsules have settled, the colour of the organic liquid is evaluated. The slurry is then stirred again for 5 minutes at a temperature 1° to 3° C. higher and the tightness of the capsules is again tested. The opening temperature can be recognized by the fact that the organic solvent becomes discolored as a result of dissolving the dyestuff issuing from the capsules. 1-Hydroxy-4-p-toluylaminoanthraquinone (="Macro-Lexviolett" B (Trade Mark)) can be used, for example, as the dyestuff which is soluble in oil and insoluble in water. A suitable organic solvent by which no dyestuff is extracted from the intact capsules even after a prolonged period of standing is ethyl acetate.

In the determination of the opening temperature by the method described, the maximum discoloration of the organic solvent is in general clearly visible within a temperature range of 1 to 3 Centigrade degrees. The higher the opening temperature of the microcapsules is, the broader is, as a rule, the temperature range within which the start of discoloration of the organic solvent phase can be observed.

If the opening temperature determined is below the desired opening temperature, hardening of the capsules is continued until the opening temperature of the capsules in the suspension is 2° to 4° C. below the desired final opening temperature of the capsules. Further hardening of the capsules is then completed by drying.

In carrying out the process according to the invention, a procedure is preferably followed in which the shell materials and core materials are emulsified in aqueous solution in the particular proportions desired, at temperatures between 20° C. and 60° C., while stirring, until an average particle size of, for example, 10 to 15 μm has been reached, and, in order to initiate coacervation, a warmed aqueous solution, which contains pre-hardening agent, is stirred in, the mixture is thereafter cooled to temperatures between 5° C. and 10°C. and, after 1 to 4 hours, an aqueous solution of the carbonyl component used for hardening is added, the pH value of the mixture is subsequently brought within the desired range by adding an aqueous base, the mixture is then stirred and the capsule suspension formed is dried with the aid of a spray-drier or in a fluidized bed.

As already mentioned, the microcapsules according to the invention can be employed for a large number of purposes. An example which may be mentioned is the use in washing agents and bath additives. Microcapsules according to the invention, which release the core material in a certain temperature range between 40° C. and 95° C. can be used in washing agents. Microcapsules which are used in bath additives have opening temperatures of between 35° and 40° C.

When the microcapsules are used for other purposes, the opening temperature is matched to the particular purpose.

The production and the properties of the microcapsules according to the invention are illustrated in the following Examples.

EXAMPLE 1

(I) Preparation of the Anionic Polymer Solution (a) Polymerization: (Copolymer (A))

225 g of acrylamide, 75 g of maleic anhydride and 3 g of azoisobutyric acid dinitrile were dissolved in 2.7 liters of ethyl acetate. The solution was freed from oxygen by evacuating the apparatus and filling it with nitrogen several times, and the solution was stirred at 60° C. for 20 hours with exclusion of oxygen. The polymer which had precipitated was filtered off, washed thoroughly with ethyl acetate and dried at 60° C. in vacuo. 273 g of a finely pulverulent polymer with a viscosity number (intrinsic viscosity) [η], determined in a 0.9% strength aqueous NaCl solution, of 0.14 [dl/g] were obtained.

(b) Hydrolysis: (Copolymer (B))

100 g of the dry polymer according to Example 1(Ia) were dissolved in 900 ml of demineralised water and the solution was heated under reflux and under normal pressure until the pH value was 4.6 (about 12 to 18 hours).

(c) Polymer Solution 150 g of dry polymer according to Example 1(Ia) were dissolved in 1,350 ml of demineralised water. The solution had a pH value of ~2.2. 300 ml of this solution were mixed with 75 ml of the hydrolysed solution according to Example 1(Ib). The mixture had a pH value of 3.4.

(II) Production of the Microcapsules 300 ml of a 10% strength aqueous solution of acid-limed pigskin gelatin and 300 ml of a 10% strength aqueous polymer solution prepared according to Example 1 (Ic) were brought together at 50° C. 240 g of the heat transfer oil "Marlotherm" (Trade Mark) S, which was stained with 0.5 g of the oil-soluble dyestuff "Macro-Lexviolett" B (=1-hydroxy-4-p-toluylamino-anthraquinone), were emulsified into the resulting clear solution until the average droplet size was 15 μm. A solution, warmed to 50° C., of B 1.3 g of carboxymethylcellulose and 1.2 g of "Tanigan" QF in 600 ml of water was then stirred in. The mixture was subsequently cooled to 8° C., while stirring. After 3 hours at 8° to 10° C., 195 g of a 0.1% strength by weight aqueous solution of glutarodialdehyde were added. The mixture was subsequently stirred for 2 to 3 minutes, the pH value was adjusted to 6.5 with 10% strength aqueous sodium hydroxide solution and the slurry was then stirred at room temperature for 16 hours.

The opening temperature of the undried capsules was 48° to 50° C.

Drying the capsules in a fluidized bed or in a spray-drier gave a free-flowing powder which, even after storage at 50° C. for a hundred days, could easily be dispersed in water and then had an opening temperature of 52° to 54° C.

In the present case, drying was carried out in a spray-drier with a two-material nozzle, using nitrogen as the propellant gas, at a hot gas temperature of 130° C. and a waste air temperature of 65° C. It was advantageous to pre-cool the capsule slurry to about 4° C.

(III) Determination of the Opening Temperature (a) In order to determine the opening temperature of the microcapsules which had been produced according to Example 1(II), which were present in suspension and which had not been first dried, 20 ml of the hardened capsule slurry were introduced into 80 ml of demineralized water. The slurry was stirred at 30° C. for 5 minutes. 1.5 ml of the capsule suspension were then poured into 20 ml of ethyl acetate, which had been warmed to 30° C., and the mixture was shaken.

After the capsules had settled, the color of the ethyl acetate solution was evaluated. No dyestuff was extracted from the still intact capsules even after a prolonged period of standing in ethyl acetate. The temperature of the suspension was then increased by in each case 1° to 2° C. and in each case was kept constant for 5 minutes, whilst stirring. The tightness of the capsules was again tested in each case by introducing 1.5 ml of the capsules into ethyl acetate at 30° to 40° C. and, after shaking and allowing the capsules to settle, evaluating the color of the ethyl acetate phase. The maximum blue coloration was observed in the temperature range from 48° to 50° C.

(b) The opening temperature of the dried microcapsules produced according to Example 1(II) was tested by suspending 4 g of the dried capsules in 100 ml of demineralized water and then proceeding as has been described under Example 1(IIIa). The opening temperature of the capsules was between 52° and 54° C.

EXAMPLES 2 TO 5

Influence of the pH value during hardening on the opening temperature of the capsules.

The procedure followed was as described in Example 1(II), but the pH value of the suspension during hardening with glutarodialdehyde was set at the pH values given in the following table by adding 10% strength aqueous sodium hydroxide solution.

TABLE 1

| Example No. | pH value | Opening temperature in °C. | | | |
|---|---|---|---|---|---|
| | | A | B | C | D |
| 2 | 6.56 | 52 | 52 | 53 | >100 |
| 3 | 6.61 | 54 | 56 | 56 | >100 |
| 4 | 6.72 | 55 | 57 | 57 | >100 |
| 5 | 6.87 | 58 | 61 | 61 | >100 |

A = slurry after the production
B = powder after the production
C = powder after storage for 6 months at room temperature
D = slurry after storage for 6 months at room temperature

EXAMPLES 6 TO 24

Effect of the concentration of glutarodialdehyde and of the nature of the tanning agent, which is active in the acid pH range, on the opening temperature of the microcapsules.

In each case 300 ml of a 10% strength by weight aqueous solution of acid-limed pigskin gelatin and 300 ml of a 10% strength aqueous polymer solution prepared according to Example 1(Ic) were brought together at 50° C. In each case 240 g of the heat transfer oil "Marlotherm" S, which had been stained with 0.5 g of the oil-soluble dyestuff "Macro-Lexviolett"B (=1-hydroxy-4-p-toluylamino-anthraquinone), were emulsified into the clear solution formed in each case, until an average droplet size of 10 μm was reached. A solution, warmed to 50° C., of 1.3 g of carboxymethylcellulose and 180 mg, corresponding to 0.3%, relative to the gelatin and polymer, of the particular tanning agent used was then stirred in.

The particular mixture was then cooled to 5° to 10° C., whilst stirring. After 3 hours at 15° to 20° C., in each case 200 ml of an aqueous glutarodialdehyde solution which contained the amount of glutarodialdehyde given in each case in the following Table 2 (150 mg=0.25%, 180 mg=0.3%, 210 mg=0.35%, 240 mg=0.4% or 270 mg=0.45% of glutarodialdehyde, relative to the amount of gelatin and polymer employed) were added. The mixture was subsequently stirred for 2 minutes and the pH value was adjusted to 6.5 with 15% strength by weight aqueous sodium hydroxide solution. The slurry was subsequently stirred for 5 minutes and then left to stand at 22° C. for 16 hours. The opening temperature of the capsules was then determined by the method given in Example 1. The experimental results are summarised in Table 2. After spray-drying, the opening temperatures of the capsules were in each case 2° to 5° C. greater than in the slurry shortly before drying.

After 3 hours at 15° to 20° C., in each case 200 ml of an aqueous glutarodialdehyde solution which contained the amount of glutarodialdehyde given in each case in the following Table 3 (150 mg ≙ 0.25%, 180 mg ≙ 0.3%, 210 mg ≙ 0.35%, 240 mg ≙ 0.4% or 270 mg ≙

TABLE 2

Effect of the concentration of glutarodialdehyde and of the nature of the tanning agent, which is active in the acid pH range, on the opening temperature of the slurry after hardening at 22° C. for 16 hours.

| Example No. | | 6 | 7 | 8 | 9 | 10 | 11 | 12 | 13 | 14 | 15 |
|---|---|---|---|---|---|---|---|---|---|---|---|
| Tannin+ | % | 0.3 | 0.3 | 0.3 | 0.3 | — | — | — | — | — | — |
| "Tanigan" QF+ | % | — | — | — | — | 0.3 | 0.3 | 0.3 | 0.3 | 0.3 | — |
| "Tanigan" PR+ | % | — | — | — | — | — | — | — | — | — | 0.3 |
| "Tanigan" PT+ | % | — | — | — | — | — | — | — | — | — | — |
| Glutaro-dialdehyde | % | 0.3 | 0.35 | 0.4 | 0.45 | 0.25 | 0.3 | 0.35 | 0.4 | 0.45 | 0.25 |
| pH during hardening | | 6.6 | 6.4 | 6.45 | 6.4 | 6.6 | 6.4 | 6.4 | 6.4 | 6.45 | 6.45 |
| Opening temperature of the slurry [°C.] | | 56 | 79 | 90 | >90 | 46 | 50 | 66 | 80 | 90 | 41 |

| Example No. | | 16 | 17 | 18 | 19 | 20 | 21 | 22 | 23 | 24 |
|---|---|---|---|---|---|---|---|---|---|---|
| Tannin+ | % | — | — | — | — | — | — | — | — | — |
| "Tanigan" QF+ | % | — | — | — | — | — | — | — | — | — |
| "Tanigan" PR+ | % | 0.3 | 0.3 | 0.3 | 0.3 | — | — | — | — | — |
| "Tanigan" PT+ | % | — | — | — | — | 0.3 | 0.3 | 0.3 | 0.3 | 0.3 |
| Glutaro-dialdehyde | % | 0.3 | 0.35 | 0.4 | 0.45 | 0.25 | 0.3 | 0.35 | 0.4 | 0.45 |
| pH during hardening | | 6.5 | 6.55 | 6.5 | 6.5 | 6.5 | 6.45 | 6.50 | 6.45 | 6.45 |
| Opening temperature of the slurry [°C.] | | 44 | 54 | 74 | 90 | 41 | 43 | 51 | 68 | 88 |

+% by weight, relative to the sum of gelatin and copolymer.

EXAMPLES 25 TO 39

Effect of the concentration of the tanning agent ["Tanigan" QF] and glutarodialdehyde on the opening temperature of the capsules.

In each case 300 ml of a 10% strength by weight aqueous solution of an acid-limed pigskin gelatin and 300 ml of a 10% strength aqueous polymer solution prepared according to Example 1(Ic) were brought together at 50° C. In each case 240 g of the heat transfer oil "Marlotherm" S, which had been stained with 0.5 g of the oil-soluble dyestuff "Macro-Lexviolett"B (=1-hydroxy-4-p-toluylamino-anthraquinone), were emulsified into the clear solution formed in each case, until an average droplet size of 10 μm was reached. A solution, warmed to 50° C., of 1.3 g of carboxymethylcellulose and the amount of tanning agent given in each case in the following Table 3 (0 g, 60 mg ≙ 0.1% and 120 mg ≙ 0.2% of "Tanigan"QF, relative to the sum of the amounts of gelatin and polymer employed) was then stirred in.

0.45% of glutarodialdehyde, relative to the amount of gelatin and polymer employed) were added.

The mixture was subsequently stirred for 2 minutes and the pH value was adjusted to 6.5 with 10% strength by weight aqueous sodium hydroxide solution. The slurry was subsequently stirred for 5 minutes and then left to stand at 22° C. for 16 hours. The opening temperature of the capsules was then determined by the method given in Example 1. The experimental results are summarized in Table 3.

TABLE 3

Effect of the concentration of the tanning agent "Tanigan" QF and glutarodialdehyde on the opening temperature of the capsule slurry.

| Example No. | | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|
| "Tanigan" QF+ | % | 0 | 0 | 0 | 0 | 0 | 0.1 | 0.1 | 0.1 | 0.1 | 0.1 | 0.2 | 0.2 | 0.2 | 0.2 | 0.2 |
| Glutaro-dialdehyde | % | 0.25 | 0.3 | 0.35 | 0.4 | 0.45 | 0.25 | 0.3 | 0.35 | 0.4 | 0.45 | 0.25 | 0.3 | 0.35 | 0.4 | 0.45 |
| pH during hardening | | 6.5 | 6.45 | 6.5 | 6.5 | 6.4 | 6.45 | 6.4 | 6.4 | 6.4 | 6.5 | 6.6 | 6.4 | 6.45 | 6.4 | 6.5 |
| Opening temperature of the slurry [°C.] | | 38 | 40 | 49 | 59 | 78 | 40 | 44 | 51 | 70 | 90 | 42 | 47 | 58 | 75 | 90 |

+% by weight, relative to the sum of gelatin and copolymer.

EXAMPLES 40 TO 53

Effect of the pH value during hardening on the opening temperature of the microcapsules.

In each case 300 ml of a 10% strength by weight aqueous solution of acid-limed pigskin gelatin and 300 ml of a 10% strength aqueous polymer solution prepared according to Example 1(Ic) were brought together at 50° C. In each case 240 g of the heat transfer oil "Marlotherm" S, which had been stained with 0.5 g of the oil-soluble dyestuff "Macro-Lexviolett" B (=1- hydroxy-4-p-toluylamino-anthraquinone) were emulsified into the clear solution formed in each case, until an average droplet size of 10 μm was reached.

A solution, warmed to 50° C., of 1.3 g of carboxymethylcellulose and 120 mg (=0.2%) of "Tanigan" QF in 600 ml of water was then stirred in. The mixture was subsequently cooled to 5° to 10° C., whilst stirring. After 3 hours at 15° to 20° C., 200 g of an aqueous solution of glutarodialdehyde which contained 120 mg ≙ 0.2% by weight or 150 mg ≙ 0.25% by weight of glutarodialdehyde, relative to the sum of the amounts of gelatin and polymer employed, were added.

The mixture was subsequently stirred for 2 minutes and the pH value was adjusted with 10% strength by weight sodium hydroxide solution to the values given in the following Table 4. The slurry was subsequently stirred for 5 minutes and then left to stand at 22° C. for 16 hours. The opening temperature of the capsules was then determined by the method given in Example 1. The experimental results are summarized in Table 4.

TABLE 4

| Effect of the pH value during hardening with glutarodialdehyde on the opening temperature of the capsule slurry. | | | | | | | | | | | | | | | |
|---|---|---|---|---|---|---|---|---|---|---|---|---|---|---|---|
| Example No. | | 40 | 41 | 42 | 43 | 44 | 45 | 46 | 47 | 48 | 49 | 50 | 51 | 52 | 53 |
| "Tanigan" QF+ | % | 0.2 | 0.2 | 0.2 | 0.2 | 0.2 | 0.2 | 0.2 | 0.2 | 0.2 | 0.2 | 0.2 | 0.2 | 0.2 | 0.2 |
| Glutarodialdehyde+ | % | 0.2 | 0.2 | 0.2 | 0.2 | 0.2 | 0.2 | 0.2 | 0.2 | 0.25 | 0.25 | 0.25 | 0.25 | 0.25 | 0.25 |
| pH during hardening | | 6.7 | 7.0 | 7.15 | 7.35 | 7.65 | 7.9 | 8.25 | 8.5 | 6.6 | 6.85 | 7.0 | 7.35 | 7.55 | 7.9 |
| Opening temperature [°C.] | | 40 | 42 | 43 | 46 | 55 | 69 | >90 | >90 | 43 | 49 | 58 | 72 | 83 | 90 |

+% weight, relative to the sum of gelatin and copolymer.

EXAMPLES 54 TO 59

Opening temperatures of gelatin/gum arabic capsules as a function of the pH value during hardening with glutarodialdehyde.

In each case 240 g of the heat transfer oil "Marlotherm" S, which had been stained with 0.5 g of the oil-soluble dyestuff "Macro-Lexviolett" B (=1-hydroxy-4-p-toluylamino-anthraquinone), were added in each case to 300 ml of a 10% strength by weight aqueous gum arabic solution of pH value 7.0 at 50° C., and the oil was emulsified-in until an average droplet size of 10 μm was reached. 300 ml of a 10% strength by weight aqueous gelatin solution at 50° C. and a solution, warmed to 50° C., of 1.3 g of carboxymethylcellulose in 600 ml of water were then slowly added successively.

In the course of 30 minutes, the pH value of the mixture was then adjusted to 4.35 by adding 5% strength by weight aqueous acetic acid solution. The formation of shells was observed under the microscope. The capsule suspension was cooled from 50° C. to 20° C. in the course of 15 minutes. As soon as the temperature reached 20° C., 12 g of a 1% strength by weight aqueous "Tanigan" QF solution were added and the mixture was cooled to 8° C. in the course of 15 minutes. After a standing time of 3 hours, without cooling, 195 g of a 0.1% strength by weight aqueous glutarodialdehyde solution were added in the course of 30 seconds.

After subsequently stirring the mixture for two minutes, the pH value was adjusted to the particular value desired, which was given in the following Table 5, with 10% strength by weight aqueous sodium hydroxide solution. The slurry was subsequently stirred for 5 minutes and then left to stand at 22° C. for 16 hours. The opening temperature of the capsules in the slurry was then determined by the method given in Example 1. After spray-drying, the opening temperature of the capsules was determined again. The experimental results are summarized in the following Table 5.

It will be understood that the specification and examples are illustrative, but not limitative of the present invention and that other embodiments within the spirit and scope of the invention will suggest themselves to those skilled in the art.

TABLE 5

| Opening temperatures of gelatin/gum arabic capsules as a function of the pH value during hardening with glutarodialdehyde. | | | | | | | |
|---|---|---|---|---|---|---|---|
| Example No. | | 54 | 55 | 56 | 57 | 58 | 59 |
| "Tanigan" QF+ | % | 0.2 | 0.2 | 0.2 | 0.2 | 0.2 | 0.2 |
| Glutarodialdehyde+ | % | 0.35 | 0.35 | 0.35 | 0.35 | 0.35 | 0.35 |
| pH value during hardening | | 6.25 | 6.6 | 6.7 | 6.9 | 7.3 | 7.45 |
| Opening temperature of the slurry [°C.] | | 42 | 50 | 52 | 63 | 85 | 93 |
| Opening temperature of the dried capsules [°C.] | | 44 | 51 | 54 | 66 | 89 | 96 |

+% by weight, relative to the sum of gelatin + gum arabic.

What is claimed is:

1. In microcapsules of the type wherein a shell wall encloses a core material, the improvement comprising said shell wall being formed of gelatin mixed with carboxymethylcellulose and anionic polymers, which polymers consists of (a) a copolymer, the structural units of which consist to the extent of 65 to 90 mole %, relative to the polymer, of randomly distributed radicals of acrylamide and to the extent of 10 to 35 mole % of radicals of maleic acid or maleic anhydride, and which have an intrinsic viscosity of 0.05 to 1.0, and (b) a copolymer, the structural units of which consist of randomly distributed polymerized radicals of acrylamide, arylic acid and maleic acid, the maleic acid radicals being at least partly present in salt form, and which has an intrinsic viscosity of 0.05 to 1.5 and contains a total of 65 to 90 mole %, relative to the polymer, of radicals of acrylamide and of acrylic acid, and 10 to 35 mole % of radicals of maleic acid, the weight ratio of a:b being 1:2 to 20:1, and said wall material being hardened with a natural or synthetic tanning agent, or a mixture thereof and glutarodialdehyde for a period of time sufficient to raise the opening temperature to a predetermined desired temperature, to form a microcapsule with a defined release temperature.

2. The microcapsules of claim 1 wherein said tanning agent is the natural tanning agent tannin.

3. The microcapsules of claim 1 wherein said tanning agent is the natural tanning agent mimosa.

4. The microcapsules of claim 1 wherein said tanning agent is the natural tanning agent quebracho.

5. The microcapsules of claim 1 wherein said tanning agent is the natural tanning agent gallic acid.

6. The microcapsules of claim 1 wherein said tanning agent is a synthetic tanning agent selected from the group consisting of methylene-linked condensation product tanning agents, aromatic sulphonic acid tanning agents and methylene-linked condensation products of aromatic sulphonic acid tanning agents.

7. The microcapsules of claim 6 wherein said tanning agents are selected from products available under the trademarks Tanigan, QF, Tanigan PR and Tanigan PT.

8. Microcapsules according to claim 1 having a release temperature in the range of between 30° C. and 150° C.

9. Microcapsules according to claim 1 having a release temperature in the range of between 35° C. to 120° C.

10. A process for the production of microcapsules according to claim 1, comprising the steps of
(a) coacervating gelatin in an aqueous medium in the presence of core material;
(b) pre-hardening the shells of the microcapsules thereby formed with a tanning agent in an acid medium and hardening with glutarodialdehyde in a weakly acid or basic medium under predetermined hardening conditions to correspond to the desired release temperature; and
(c) drying the hardened microcapsules.

11. The process of claim 10 wherein the hardening step is accomplished by addition of the glutarodialdehyde one to four hours after the prehardening step is accomplished.

12. A process according to claim 10 in which the tanning agent is tannin, mimosa, quebracho, gallic acid, a methylene-linked condensation product of a hydroxyarylsulphone and an aromatic sulphonic acid or a methylene-linked condensation product of aromatic sulphonic acids.

13. A process according to claim 10 in which the gelatin is mixed with gum arabic, carboxymethylcellulose and an anionic polymer.

14. The process of claim 10 wherein coacervation is initiated by cooling the medium, changing the pH of the medium, diluting the medium or a combination thereof.

15. The process of claim 10 wherein
pre-hardening takes place in an acid medium with a pH between 3 and 6 and at a temperature in the range of 5° C. to 70° C,
the hardening takes place in a basic or weakly acid medium with a pH from about 5.5 to about 11 and at a temperature from about 0° C. to about 70° C.

16. The process of claim 10 wherein
the pre-hardening pH is from about 3.5 to about 5 and the temperature is from about 5° C. to about 80° C., and
the hardening pH is from about 6.0 to about 10 with a temperature from about 20° C. to about 60° C.

17. A process for the production of microcapsules of the type wherein a shell wall encloses a core material, comprising the steps of coacervating gelatin in an aqueous medium in the presence of the core material by mixing the gelatin with a polymer of acrylamide and maleic anhydride, in approximately equal amounts by weight in about a 10% aqueous solution at 50° C.; emulsifying the core material in the gelatin solution until the average droplet is size 10 to 15 μm, and thereafter, adding a solution, warmed to 50° C., of carboxymethylcellulose;
pre-hardening the shells of the microcapsules by adding, as a tanning agent, Tannigan QF in acidic water with stirring, and thereafter cooling the mixture to between 5° C. and 10° C. and stirring for three hours;
hardening the shell of the microcapsule by adding to the mixture an aqueous solution of glutarodialdehyde, and stirring for 2 to 3 minutes, thereafter adjusting the pH value to 6.5 with 10% strength aqueous sodium hydroxide solution and stirring the resulting slurry at room temperature for 16 hours; and thereafter
drying the resulting capsules in a fluidized bed or in a spray-drier to give a free-flowing powder which is easily dispersed in water.

18. The process of claim 17 wherein the
amount of glutarodialdehyde added ranges from about 0.25 to about 0.45 percent by weight relative to the sum of gelatin and copolymer weights.

* * * * *